United States Patent [19]
Cherepenin et al.

[11] Patent Number: 6,167,300
[45] Date of Patent: Dec. 26, 2000

[54] ELECTRIC MAMMOGRAPH

[75] Inventors: Vladimir Alexeevich Cherepenin; Alexandr Vladimirovich Korjenevsky, both of Moscow, Russian Federation

[73] Assignee: TCI Incorporated

[21] Appl. No.: 09/264,594

[22] Filed: Mar. 8, 1999

[51] Int. Cl.[7] ............................................. A61B 5/05
[52] U.S. Cl. ........................... 600/547; 128/920; 324/717
[58] Field of Search ........................... 600/547; 128/920; 324/600, 713, 717

[56] References Cited

U.S. PATENT DOCUMENTS

| | | | |
|---|---|---|---|
| 4,263,920 | 4/1981 | Tasto et al. | 600/547 |
| 4,486,835 | 12/1984 | Bai et al. | 378/21 |
| 4,539,640 | 9/1985 | Fry et al. | 600/547 |
| 5,284,142 | 2/1994 | Goble et al. | 600/547 |
| 5,351,697 | 10/1994 | Cheney et al. | 600/547 |

OTHER PUBLICATIONS

Nowakovsky, A., J. Wortek, and J. Stelter, "A Technical University of Gdansk Electroimpedance Mammograph," Proc. IX Int. Conf. Electrical Bio–Impedance, Heidelberg, 1995, pp. 434–437.

Wortek, J.,J. Stelter, A. Nowakovsky, "Impedance mammograph 3D phantom studies," Proc. X Int. Conf. Electrical Bio–Impedance, Barcelona, 1998, p. 521–524.

*Primary Examiner*—Ruth S. Smith
*Attorney, Agent, or Firm*—Robert W. Becker & Associates

[57] ABSTRACT

The electric mammograph is an electrical impedance tomograph device for obtaining three-dimensional images of the conductivity distribution in biological tissues. A planar array of electrodes is put in contact with the tissues of interest. An AC source is connected to a single remotely attached electrode and to one of the planar array electrodes. Potential differences between the at rest electrodes in the planar array and a second remote at rest electrode are measured. The images are reconstructed using a modified back projection method.

7 Claims, 5 Drawing Sheets

ELECTRIC MAMMOGRAPH

FIELD OF TECHNOLOGY

The invention is in the field of medical tomography, and in particular relates to a method and apparatus for the visualization and diagnosis of pathologic changes in breast tissues and other organs near the surface of the human body.

BACKGROUND OF THE INVENTION

It is known that electrical conductivity of many tumors, and in particular the malignant tumors of the mammary gland, significantly differs from the conductivity of surrounding sound tissues. This fact may be used for the detection and localization of such tumors.

Some devices are known for visualizing the spatial distribution of conductivity (impedance) in the human body, e.g., electrical impedance tomographs. (A. V. Korjenevsky, Yu. S. Kultiasov, V. A. Cherepenin, "Method of obtaining of tomographic image of a body and electrical impedance tomograph," International application PCT/RU97/00398.) In an electrical impedance tomograph, the source of alternating electric current is connected to pairs of electrodes placed along a line on the surface of a body and measurements of the potential differences are made on the other pairs of electrodes. The results of measurements obtained from various combinations of electrodes are used to reconstruct the conductivity distribution with the help of a computer. A three-dimensional distribution of conductivity, however, is not possible with this type of tomograph. Furthermore, its resolution falls significantly from the periphery to the center of contour of the electrodes. Consequently, it is not an adequate device for the diagnosis of mammary gland tumors.

An electroimpedance mammograph device, purporting to yield a three-dimensional impedance distribution has also been described. (A. Nowakovsky, J. Wortek, and J. Stelter, "A Technical University of Gdansk Electroimpedance Mammograph," Proc. IX Int. Conf. Electrical Bio-Impedance, Heidelberg, 1995, p. 434–437; J. Wortek, J. Stelter, A. Nowakovsky, "Impedance mammograph 3D phantom studies," Proc. X Int. Conf. Electrical Bio-Impedance, Barcelona, 1998, p. 521–524.) This device contains a compact set of electrodes that are placed on the inner surface of a rigid hemisphere, multiplexers that are connected to the source of alternating electric current, and a device for measuring the potential difference between various pairs of electrodes. The measured potential differences are sent to a computer to reconstruct and display the three-dimensional impedance distribution inside the hemisphere. The serviceability of this device based on actual measurements on the human body have not yet been published.

A number of limitations for this device are apparent. The arrangement of electrodes on the hemisphere surface limits the application of the device because the contact with all the electrodes can be provided only for a breast of a definite size. The device also has no means to measure the quality of each contact, nor any means to correct the reconstruction calculations if any of the electrodes have insufficient contact with the body. This decreases the validity of the data. The electric current source and the measuring device are connected to pairs of electrodes placed on the hemisphere, requiring four multiplexers. When the number of electrodes is large, these multiplexers become the most complicated and expensive parts of the device. These multiplexers are also the largest source of spurious signals due to channel-to-channel crosstalk. Only 64 electrodes were used in the prototype. This is obviously insufficient for obtaining satisfactory resolution. However, further increasing this number is problematical because of the difficulty of commutation by the chosen measuring circuit.

When a safe level of electrical current is used, the measured potential differences are small because of the small distances between electrodes. This decreases the signal-to-noise ratio and the display quality. This effect only gets worse with an increasing number of electrodes. The algorithm for image reconstruction is based on the perturbation method. It requires a calculation time of ten minutes on a workstation for a system of 64 electrodes (Nowakovsky). For 180 electrodes, the minimum necessary for practical applications, about ten hours are required for the calculations based on the estimations of the authors. This amount of time is not feasible for clinical practice.

Other attempts at obtaining three-dimensional electrical impedance images of a body have involved multi-dimensional electrode arrays that surround or partially surround the object being imaged. The reconstruction algorithms used and the methodology of making measurements were also different than those of the present invention. These efforts include U.S. Pat. Nos. 5,284,142, 5,351,697, 4,263,920, 4,486,835, and 4,539,640.

A goal of the present invention is to provide a new method and apparatus for electric mammography with greater reliability and accuracy of measurements, higher resolution, and increased computational speed. This invention is particularly applicable to the clinical diagnosis of breast tumors and other subsurface areas.

SUMMARY OF THE INVENTION

The electric mammograph is a device for the measurement and three-dimensional (3-D) reconstruction of the conductivity distribution in biological tissues for clinical diagnoses. It consists of a compact array of electrodes positioned over the tissue being measured, two additional electrodes spaced apart from the array of electrodes, a source of alternating (AC) current, a means to measure potential difference, and computing means to reconstruct and visualize the resulting conductivity distribution.

BRIEF DESCRIPTION OF THE DRAWINGS

The invention is illustrated in the following drawings.

DESCRIPTION OF THE PREFERRED EMBODIMENT

Figure 1:
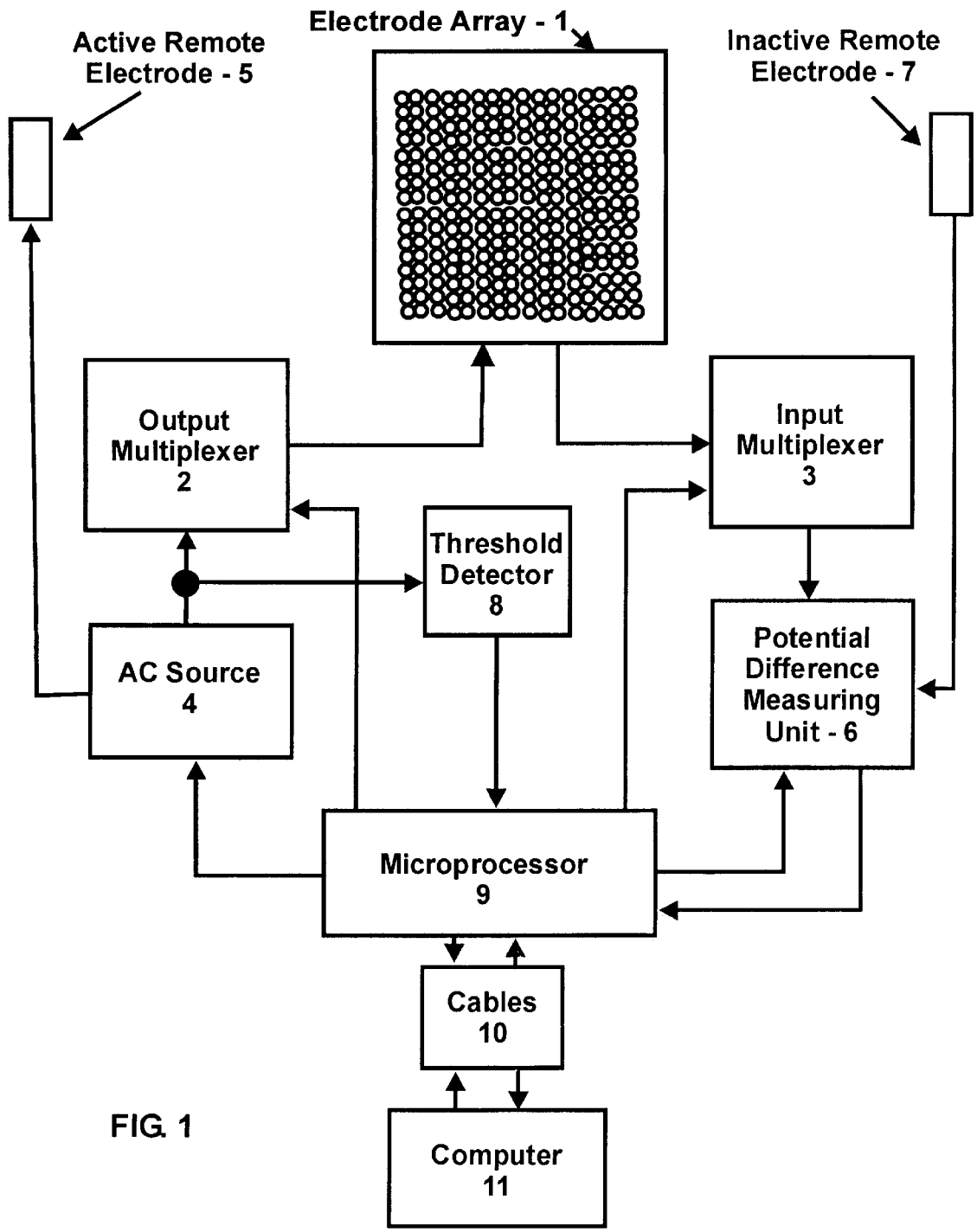
FIG. 1 is a block diagram of the electric mammograph.

A block diagram of the components of the electric mammograph is shown in FIG. 1. A compact array of cylindrical protruding electrodes 1 is arranged in a rigid dielectric plane. The example shown has 256 electrodes. The output multiplexer 2 is connected to the electrode array 1 and is the means by which the alternating current (AC) source 4 is connected to one of the cylindrical electrodes in the array. The input multiplexer 3 serves to connect one of the non-activated or "rest" electrodes of the array to the potential difference measuring unit 6. The microprocessor 9 and the computer 11, connected via cables 10, determine which electrode is activated and which of the rest electrodes is being measured at any given time.

Figure 2:
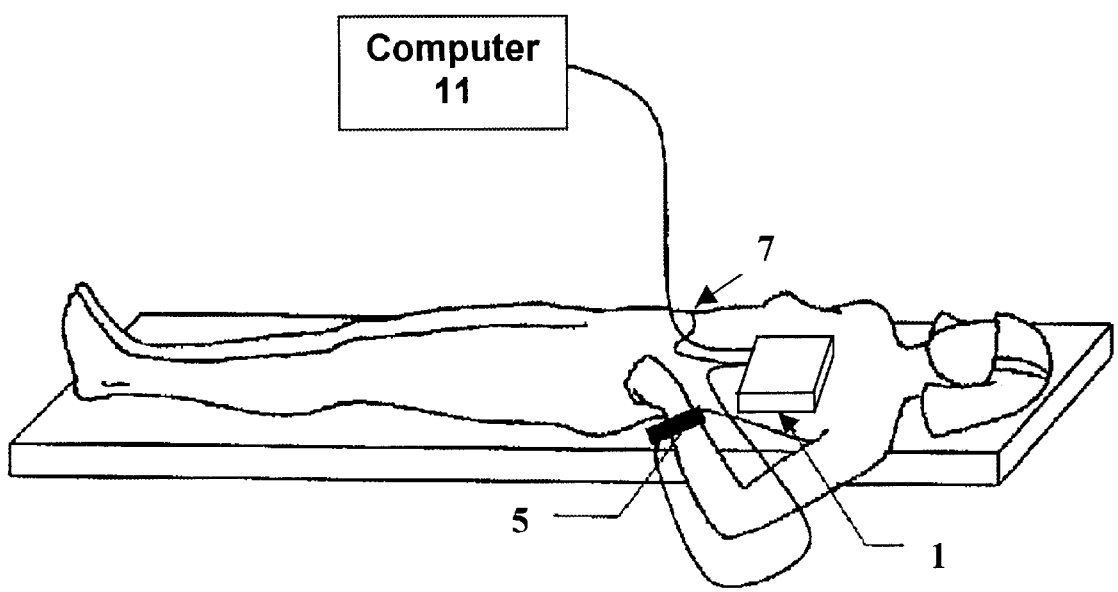
FIG. 2 shows the arrangement of the apparatus when conducting a mammograph examination.

Two single remote electrodes, 5 and 7, are attached to the extremities of the patient. One remote electrode 5 is connected directly to the AC source. The other remote electrode 7 is connected directly to the potential difference detector 6. The AC source is connected to a voltage threshold detector 8. The operation of the electric mammograph is controlled by a microprocessor/computer means. It gets inputs from the potential difference detector 6 and the threshold detector 8 and outputs to the two multiplexers 2, 3, the potential difference detector, and the AC source. The first remote electrode 5 connected to the AC source and the second remote electrode 7 are located on a patient's extremities, e.g., one on each wrist as shown in FIG. 2 (the second remote electrode 7, connected to the patient's right wrist, is not shown).

In the prior art methods of obtaining a tomographic image of a human body, a series of contact electrodes were placed on the surface of the patent's body. A source of electric current was connected sequentially to pairs of electrodes causing current to flow through the body. Measurements were then made of potential differences between pairs of other "non-activated" electrodes.

In the present invention, the output multiplexer 2 switches a single lead from the AC source to "activate" a single electrode in the electrode array I at a time, instead of activating pairs of electrodes in prior art devices. The second "activated" electrode is the remote electrode 5 that is always "on". Switching a single lead at a time reduces the spurious couplings arising from channel-to-channel penetration of signals in the multiplexer. It also simplifies the device and reduces its cost. The same is true for the input multiplexer 3. The potential difference detector measures the difference between the selected array electrode and the remote rest electrode 7. For a given rest electrode, the output multiplexer 2 sequences through all the other electrodes in the compact set while the potential difference detector makes its measurements. Then the rest electrode is switched and the output multiplexer sequence repeated.

Using the two singular electrodes 5, 7 also increase the amplitude of the measured signals due to the increased distance between the points where the potentials are measured. This increases the signal-to-noise ratio and the accuracy of the measurements. The distance of these singular electrodes from the electrode array allows one to assume that the unperturbed equipotential surfaces of electric field are spherical in the examination area. It simplifies and speeds up the conductivity reconstruction calculations.

A modified form of the method of back projection along equipotential surfaces of the electric field is used to reconstruct the 3-D conductivity distribution. It is assumed that in the case where the electric current is injected through one of the electrodes of the compact set of electrodes arranged in a planar array and the remote common electrode, equipotential surfaces near the two-dimensional set of electrodes are spherical. The procedure of back projection is reduced to the following. For some point with coordinates (X,Y,Z) inside the object under visualization, the distance is determined between this point and the injecting electrode of the compact array. This distance is equal to the radius r of the equipotential surface containing the point where the conductivity is reconstructed. Knowing this radius, it is possible to determine the line of intersection of the equipotential surface with the surface on which the electrodes are arranged. When the electrodes are arranged on the plane, given by equation z=0, this line is the circle lying in the (x, y) plane having its center at the point where the injecting electrode is located, and having radius r. Conductivity S (in arbitrary units) at the chosen point is calculated according to the equation:

$$S(x, y, z) = 1 + W_1(z) \sum_i \frac{1}{\int_{L(x,y,z,i)} W_2(l) dl} \int_{L(x,y,z,i)} W_2(l)(E_r(l) - E_m(l))/E_r(l) dl$$

where i—is the number of the injecting electrode, L(x,y,z, i)—is the line of intersection of the equipotential surface with the surface on which the electrodes are arranged (circle with radius r). The components of the electric field vector $\vec{E}_m$ are first calculated at the nodes of the grid between the electrodes as the potential differences between adjacent electrodes in the x and y directions. Then these components are linearly interpolated to the current point of integration on the line L and the magnitude of this vector $E_m$ is calculated. The reference intensity of the electric field $E_r$ corresponds to a homogeneous medium and is calculated numerically. Weighting coefficient $W_1(z)$ corrects the decrease of sensitivity with depth. In the present invention, the empirical equation $W_1(z+\alpha)/(z+\beta), \alpha<<\beta$ is used for it. The weighting coefficient $W_2$ provides a relatively greater contribution to the calculated conductivity of those points on line L, which are located closer to the point at which the conductivity is reconstructed. In the present device, the equation: $W_2=1/R_4=1/((x-x_l)^2+(y-y_l)^2+z^2)^2$ is used, where R is the distance between the point where the conductivity is reconstructed and the current point on the line along which integration is being carried out; the index l refers to the coordinates of this point.

The method of back projection is the fastest method used in electrical impedance tomography reconstruction. Its use, however, for reconstructing the static conductivity distribution for the 3-D case is only possible by a proper choice of the projected values. In addition, the synthesized reference data set $E_r$ must be used. This is obtained by approximating the real measured potentials according to the method of Korjenevsky. (A. V. Korjenevsky, Yu. S. Kultiasov, V. A. Cherepenin, "Method of obtaining of tomographic image of a body and electrical impedance tomograph," Russian Federation patent application N 96123647/14.)

In many cases it is difficult to obtain sufficient contact of all the electrodes with the patient's body. Consequently, the threshold detector 8 of the output voltage is used to determine whether the electrode being measured at any particular moment has sufficient contact with the body. The compact set of electrodes is arranged on a rigid dielectric plane and every electrode is a conducting protrusion from the plane. This arrangement permits an examination of a mammary gland regardless of its size. During an examination, this plane of electrodes is pressed against the breast, flattening it toward the chest. This increases the number of electrodes having contact with the body and decreases the thickness of the tissue layer to be measured. The protrusion of the electrodes improves their electrical contact with the body.

One or more of the electrodes on the periphery of the plane may not have contact with the body, depending on the size of the examined object. These electrodes are detected with the help of the threshold detector of the output voltage mentioned above. The values of the potential differences measured from electrodes that have insufficient body contact cannot be used directly in the process of conductivity reconstruction. Instead, values of potential differences calculated on the assumption of a homogeneous conductivity distribution are used.

Besides the useful potential differences caused by the current flow, there are also galvanic potential differences between electrodes. The component for measuring the potential difference 6 is only sensitive to the alternating current component and, consequently, is not disturbed by the presence of these constant galvanic potential differences. However, due to the differences in galvanic potentials of different electrodes, the input voltage varies by a jump when the input multiplexer 3 is switched. These jumps produce a transient that influences the results of the measurements. This influence increases when the time interval between the switch and the start of the potential difference measurement decreases. Therefore, to decrease the error while keeping the total duration of the measurements constant, the input multiplexer 3 should switch the device for measuring the potential difference 6 to the next electrode only after the output multiplexer 2 completes the total cycle of switches of the AC source to all other electrodes.

FIG. 2 shows the arrangement of the various components of the electric mammograph used to take measurements. With the help of the output multiplexer, the control unit connects the source of AC current to one of the electrodes of compact set 1 according to commands from the computer 11. AC current of approximately 1 mA and a frequency of 10 kHz flows through the circuit, i.e., from the AC source to the multiplexer, to the electrode of set 1, through the patient's body to the remote rest electrode 5. With the help of the input multiplexer, the microprocessor connects one of the rest electrodes from set 1 to the potential difference detector. It measures the amplitude of the alternating voltage between the electrode from set 1 and the remote activated electrode 7. This measurement is sent in digital code to the microprocessor, which passes it to the computer 11.

Figure 3:
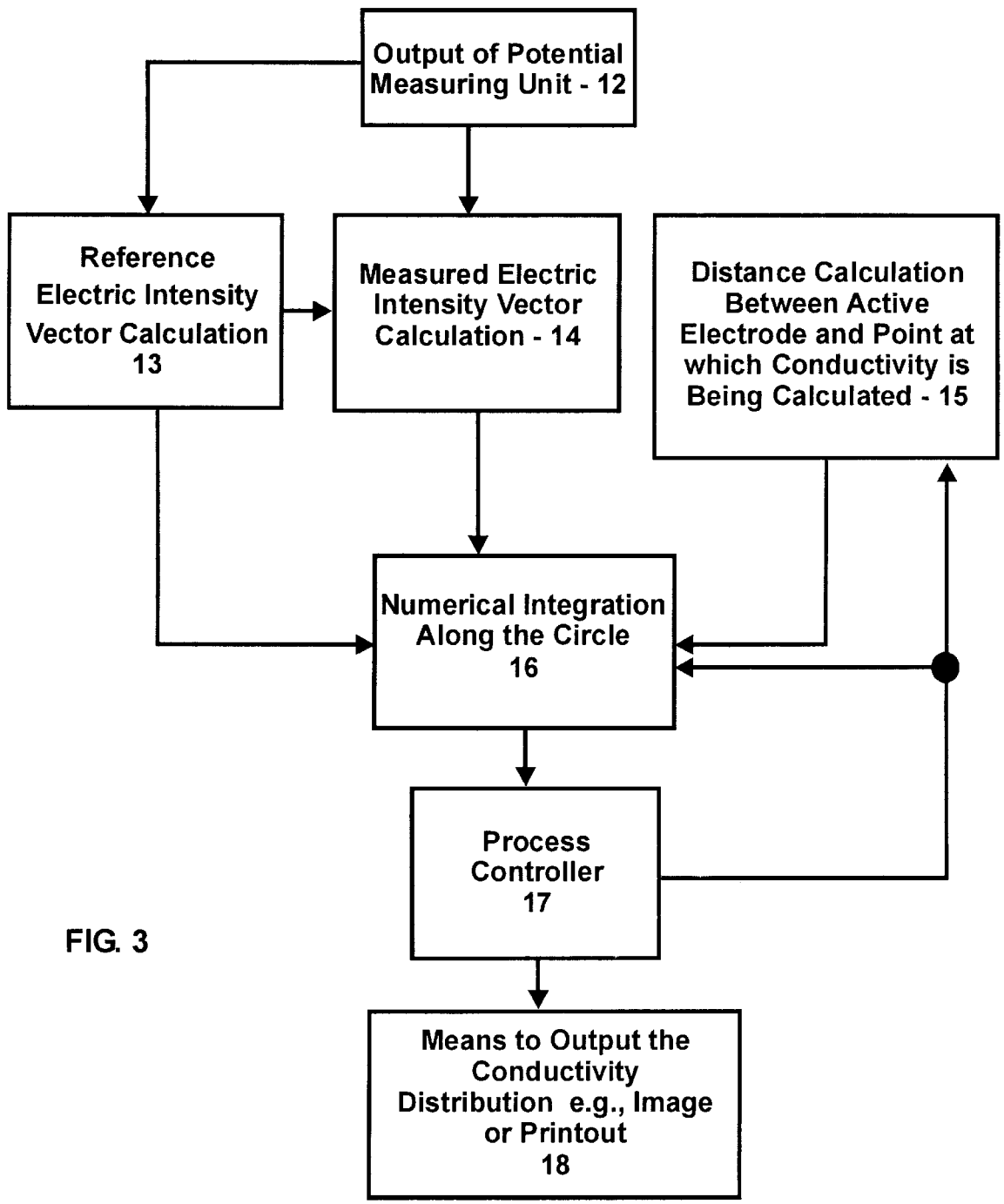
FIG. 3 is a block diagram of the algorithm used for the three-dimensional conductivity distribution reconstruction.

The measured data are used to reconstruct a 3-D conductivity distribution with the help of the algorithm shown in block diagram form in FIG. 3. In block 12 the measured potentials of the electrodes from the compact set, received through the connection line 10, are used for synthesis of the reference set of potentials corresponding to a body with homogeneous conductivity. An approximation by the method of least squares described in Russian Patent N 96123647/14 is used. Only those potentials obtained from electrodes with good body contact are used. In blocks 13 and 14, components of the electric intensity vector are calculated for the reference and measured data set by subtraction of the values of potentials on adjacent electrodes for each variant of connection of the current source. In the last case, corresponding potentials from the reference set are used instead of the potentials of those electrodes with insufficient contact.

In block 15 the distance is calculated between the activated electrode in the compact set and the point at which the conductivity is being reconstructed. This distance determines the radius of a circle that represents the line of intersection of the equipotential surface with the plane on which the electrodes are arranged and along which it is necessary to carry out weighted averaging. The electric intensity for the measured and the reference data set are calculated after the linear interpolation of the corresponding components of vectors, calculated in blocks 13 and 14. The relative difference of the electric intensities for the reference and measured data sets are multiplied by the weight function $1/R^4$, where R is the distance between the point where the conductivity is reconstructed and the current point on the line along which averaging is being carried out.

In block 16 the obtained value is numerically integrated along the circle. These operations are repeated for all points where the conductivity is to be reconstructed and for all variants of the activated electrodes. This process is controlled by block 17. The result of these calculations, after adding a unit to obtained values, represents a 3-D distribution of the conductivity normalized on the average value. The result can be displayed on screen or printed out. Block 18 contains the software and hardware used to carry out these functions.

Figure 4:
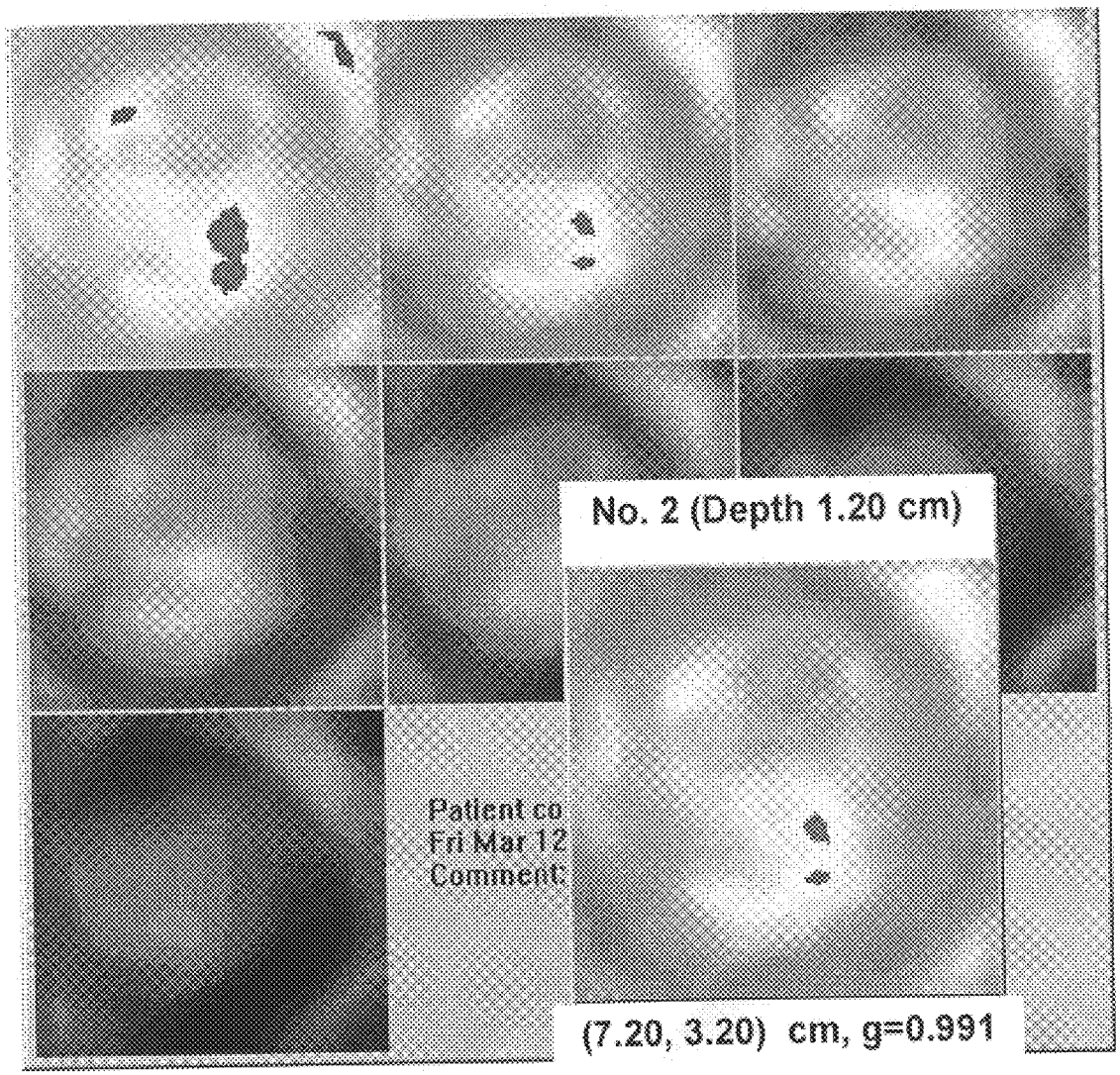
FIG. 4 is a photograph of the apparatus
Figure 5:
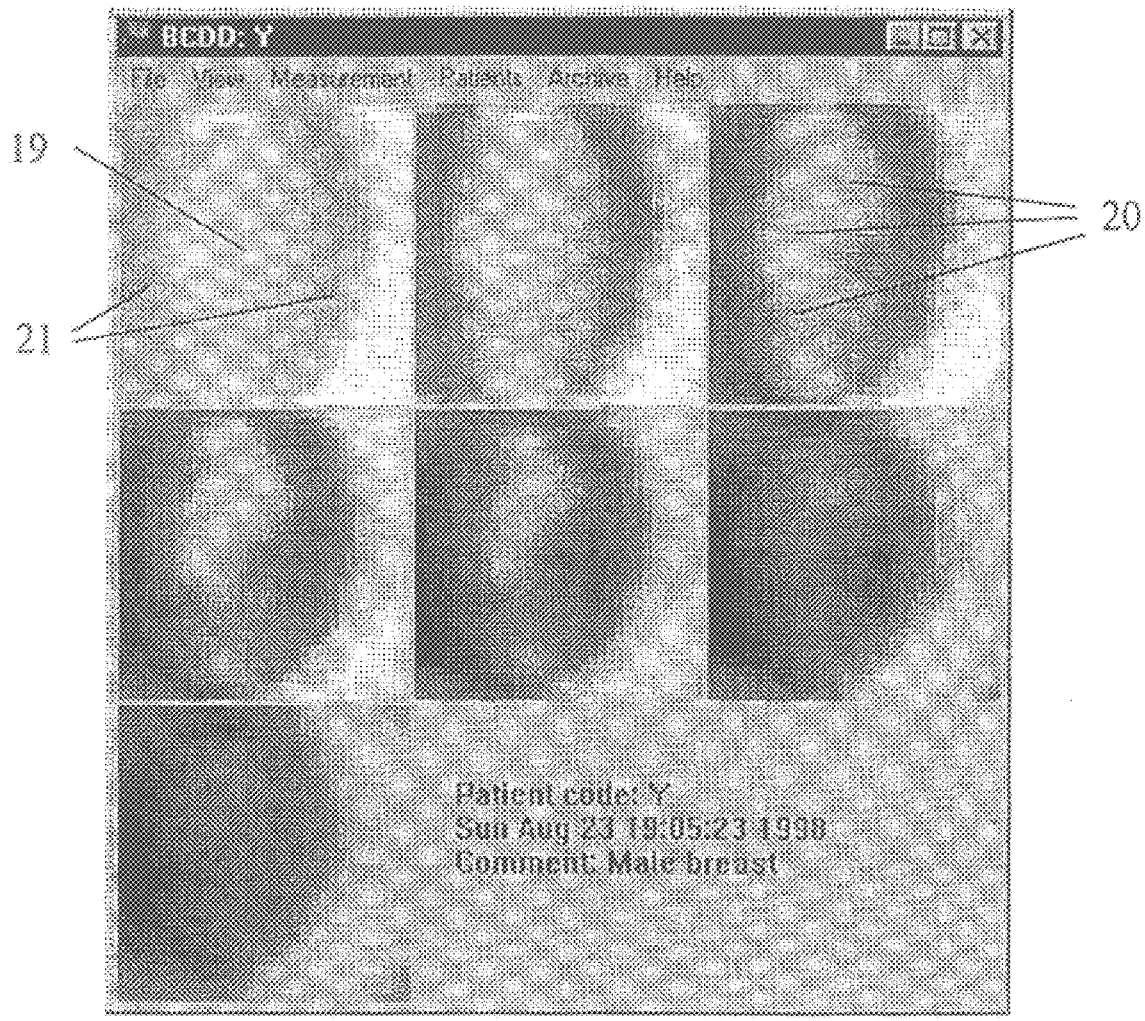
FIG. 5 is a sample electric mammogram.

The external appearance of the electric mammograph without the computing unit is shown in FIG. 4. FIG. 5 shows an electric mammogram obtained by the invention. The mammogram represents a set of seven images of breast cross-sections parallel to the plane on which the electrodes are arranged. The depth of the cross-sections increases from left to right and from up to down with 8 mm steps. On the image one can clearly see the nipple 19, the ribs 20, and the boundary 21 between areas with and without sufficient electrode contact with the body.

What we claim is:

1. A method of constructing a three-dimensional conductivity distribution for a biological tissue mass, said method comprising the steps of:

(a) applying a source of alternating current (AC) to a first activated electrode of a compact set of electrodes arranged in a planar array, said compact set of electrodes being in contact with the surface of said biological tissue mass, and to a single remotely located active electrode in contact with said biological tissue mass but at some distance from said compact set of electrodes, thereby setting up an electric field in said biological tissue;

(b) measuring a potential difference between a first inactive (at rest) electrode of said compact set and a single remotely located inactive electrode, said single remote inactive electrode being remotely located with respect to both said compact set of electrodes and said single remote active electrode;

(c) switching said AC source to activate successively all of the electrodes of said compact set of electrodes except said inactive electrode of step (b) and measuring a potential difference between said inactive electrode in (b) and said single remote inactive electrode for each activated electrode in turn to thereby obtain a first set of potential difference measurements for each successively activated electrode in said compact set of electrodes;

(d) switching the electrode to be measured in said compact set of electrodes to a second inactive electrode;

(e) switching said AC source to activate successively every other electrode in said compact set of electrodes, and measuring a potential difference between said second inactive electrode and said single remote inactive electrode in turn to thereby obtain a second set of potential difference measurements for each activated electrode;

(f) continue switching the inactive electrode in said compact set of electrodes as in steps (d) and (e), activating successively the remaining electrodes in said compact set of electrodes, and measuring the potential difference between the selected inactive electrode and said single inactive remote electrode in turn until all combinations of said compact set of electrodes have been measured; and (g) reconstructing a three-dimensional conductivity distribution of said biological tissue mass using a back projection calculation method.

2. The method of claim 1, including measuring an output voltage of said AC source for each combination of active electrodes to determine whether any particular electrode of said planar array had sufficient contact with said biological tissue to give a meaningful measurement.

3. The method of claim 2, including calculating the values of potential differences for those electrodes having insufficient contact with said biological tissue mass based on the assumption of a homogeneous conductivity distribution rather than using the actual measured potential differences.

4. The method of claim 1, including using the weighting coefficient of $1/R^4$ in the back projection calculation of step (g), where R is the distance between a point where conductivity is being reconstructed and a current point on a line along which averaging is being carried out.

5. An apparatus for producing a three-dimensional image of the conductivity distribution in a biological tissue mass, said apparatus comprising:

a) a plurality of individual electrodes disposed in a rigid planar array and adapted to be placed in contact with said biological tissue mass, said planar array having one active electrode at any given time, the remaining electrodes being inactive;

b) a single remote active electrode located at some distance from said planar array and adapted to be placed in contact with said biological tissue mass;

c) a single remote inactive electrode located at some distance from said planar array and from said single remote active electrode and adapted to be placed in contact with said biological tissue mass;

d) an alternating current (AC) source connected to one of the electrodes (active electrode) in said planar array, thereby making it an active electrode, and continuously connected to said single remote active electrode;

e) an output multiplexer to successively switch said AC source to other electrodes in said planar array making them active electrodes in turn;

f) means to measure a potential difference between the inactive electrodes in said planar array and said single inactive remote electrode;

g) an input multiplexer to successively switch said means for measuring said potential difference between said inactive electrodes in said planar array and said single remote inactive electrode;

h) means coupled to said input and output multiplexers for sequencing said AC source through said planar array electrodes while taking potential difference measurements;

i) means for recording said potential difference measurements;

j) means for calculating and reconstructing a three-dimensional conductivity distribution of said biological tissue mass; and k) means for displaying an image of said three-dimensional conductivity distribution.

6. The apparatus of claim 5, further including a means for determining whether any particular electrode of said planar array has sufficient contact with said biological tissue to give a meaningful measurement.

7. The apparatus of claim 5, wherein said planar array of electrodes is arranged on a rigid dielectric plane and the conducting portion of each electrode protrudes from said plane.

* * * * *